United States Patent
Gradon et al.

(10) Patent No.: US 6,662,803 B2
(45) Date of Patent: Dec. 16, 2003

(54) NASAL MASK

(75) Inventors: Lewis George Gradon, Auckland (NZ); Nicholas Charles Alan Smith, Auckland (NZ); Alastair Edwin McAuley, Auckland (NZ); Mark Joseph Haycock, Auckland (NZ); Chris Earl Nightingale, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 09/881,394

(22) Filed: Jun. 14, 2001

(65) Prior Publication Data

US 2002/0014241 A1 Feb. 7, 2002

(30) Foreign Application Priority Data

| Jun. 14, 2000 | (NZ) | 505154 |
| Jun. 14, 2000 | (NZ) | 505155 |
| Jun. 14, 2000 | (NZ) | 505156 |
| Nov. 16, 2000 | (NZ) | 508218 |
| Nov. 16, 2000 | (NZ) | 508219 |
| Nov. 27, 2000 | (NZ) | 508433 |
| Dec. 20, 2000 | (NZ) | 509039 |

(51) Int. Cl.$^7$ ............................................. A62B 18/02
(52) U.S. Cl. ..................... 128/205.25; 128/206.16; 128/206.17; 128/206.18; 128/207.13
(58) Field of Search ................. 128/205.25, 204.14, 128/206.15, 206.17, 206.18, 207.13

(56) References Cited

U.S. PATENT DOCUMENTS

| 2,944,547 A |   | 7/1960  | Ziherl et al. |            |
| 4,784,129 A | * | 11/1988 | Garraffa      | 128/200.29 |
| 4,981,134 A | * | 1/1991  | Courtney      | 128/206.15 |
| 4,989,596 A | * | 2/1991  | Macris et al. | 128/201.28 |
| 5,117,821 A | * | 6/1992  | White         | 128/206.12 |
| 5,372,130 A | * | 12/1994 | Stern et al.  | 128/205.25 |
| 5,438,981 A | * | 8/1995  | Starr et al.  | 128/205.24 |
| 5,558,466 A | * | 9/1996  | Kuo et al.    | 405/186    |
| 5,560,354 A | * | 10/1996 | Berthon-Jones et al. | 128/204.18 |
| 5,647,357 A | * | 7/1997  | Barnett et al. | 128/205.25 |
| 5,657,752 A | * | 8/1997  | Landis et al. | 128/201.28 |
| 5,662,101 A | * | 9/1997  | Ogden et al.  | 128/202.27 |
| 5,746,201 A | * | 5/1998  | Kidd          | 128/205.25 |
| 5,896,857 A | * | 4/1999  | Hely et al.   | 128/205.24 |
| 6,123,071 A | * | 9/2000  | Berthon-Jones et al. | 128/204.18 |
| 6,125,849 A | * | 10/2000 | Williams et al. | 128/206.12 |
| 6,460,539 B1 | * | 10/2002 | Japuntich et al. | 128/205.27 |

FOREIGN PATENT DOCUMENTS

| EP | 0697225 A2 | * | 2/1996 |
| EP | 958841 |   | 11/1999 |
| WO | WO 9834665 |   | 8/1998 |
| WO | WO 9848879 |   | 11/1998 |
| WO | WO 0078382 |   | 12/2000 |

* cited by examiner

Primary Examiner—Weilun Lo
Assistant Examiner—Michael Mendoza
(74) Attorney, Agent, or Firm—Trexler, Bushnell, Giangiorgi, Blackstone & Marr, Ltd.

(57) ABSTRACT

A CPAP system is described for improved respiratory therapy of patients. In particular a patient interface is disclosed with an outlet vent with lower noise levels and more diffused outlet flow over prior art outlet vents. The outlet vent includes a main vent which is diffused and muffled and a higher resistance vent provided in case the main vent is blocked. The outlet vent is removable for easy maintenance and provides indication to the user when maintenance is required. The outlet vent described may be used on nasal masks, mouthpieces and patient interfaces generally.

16 Claims, 8 Drawing Sheets

NASAL MASK

FIELD OF INVENTION

This invention relates to patient interfaces particularly though not solely to nasal mask for use in providing CPAP therapy to patients suffering from obstructive sleep apnoea (OSA).

BACKGROUND OF THE INVENTION

In the art of respiration devices, there are well known a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory devices has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

Where such masks as those used above are used in respiratory therapy, in particular treatment of obstructive sleep apnea (OSA) using Continuous Positive Airway Pressure (CPAP) therapy, there is generally provided in the art a vent for washout of the bias flow or expired gases to the atmosphere. Such a vent may be provided for example, as part of the mask, or in the case of some respirators where a further conduit carries the expiratory gases, at the respirator. The washout of gas from the mask is essential to ensure that carbon dioxide build up does not occur over the range of flow rates. In the typical flow rates in CPAP treatment, usually between 4 cm $H_2O$ to 20 cm $H_2O$, prior art attempts at such vents have resulted in excessive noise causing irritation to the user and concentrated flows of gases irritating any bed partners.

Various approaches have been developed in the prior art to attempt to reduce the noise when CPAP therapy is provided. For example, in PCT Patent Application No. WO98/34665 it has been proposed that the vent include a resilient plug with rounded edges at the apertures to reduce noise. In PCT patent application no WO00178382 a vent is provided with a semi annular flap. However, these prior art methods are not entirely satisfactory in eliminating the extra noise created by a vent at the mask.

SUMMARY OF INVENTION

It is an object of the present invention to attempt to provide a nasal mask which goes some way to overcoming the abovementioned disadvantages in the prior art or which will at least provide the industry with a useful choice.

Accordingly in a first aspect the invention consists in a device for delivering a supply of gases to a user comprising:

a patient interface, in use in fluid communication with said supply of gases and supplying said gases to said user, and outlet means integrated with or attached to said patient interface including at least one outlet vent and a removable diffusing member in use covering said vent, said removable member in use diffusing a substantial portion of the expired gases of said user.

In a second aspect the present invention consists in a CPAP system for delivering gases to a user including a pressurised source of gases, transport means in fluid communication with said pressurised source adapted to convey said gases, and a patient interface in fluid communication with said transport means in use delivering said gases to said user, said patient interface including:

outlet means having at least one outlet vent, and a removable diffusing member covering said vent, said outlet means in use passing a substantial portion of the expired gases of said user.

In a third aspect the present invention consists in removable diffusing member for a gases delivery patient interface, said patient interface including at least one vent, said removable member adapted to be juxtaposed in use on or over a vent, said removable member adapted to in use pass a substantial portion of expired gases from a user flowing out from a vent.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention provides improvements in the field of CPAP therapy. In particular an outlet is described which is quieter and has a more diffused outlet flow. It will be appreciated that the nasal mask as described in the preferred embodiment of the present invention can be used in respiratory care generally or with a ventilator but will now be described below with reference to use in a humidified CPAP system. It will also be appreciated that the outlet vent described is equally applicable to all forms of patent interface, in particular a mouth piece.

Figure 1:
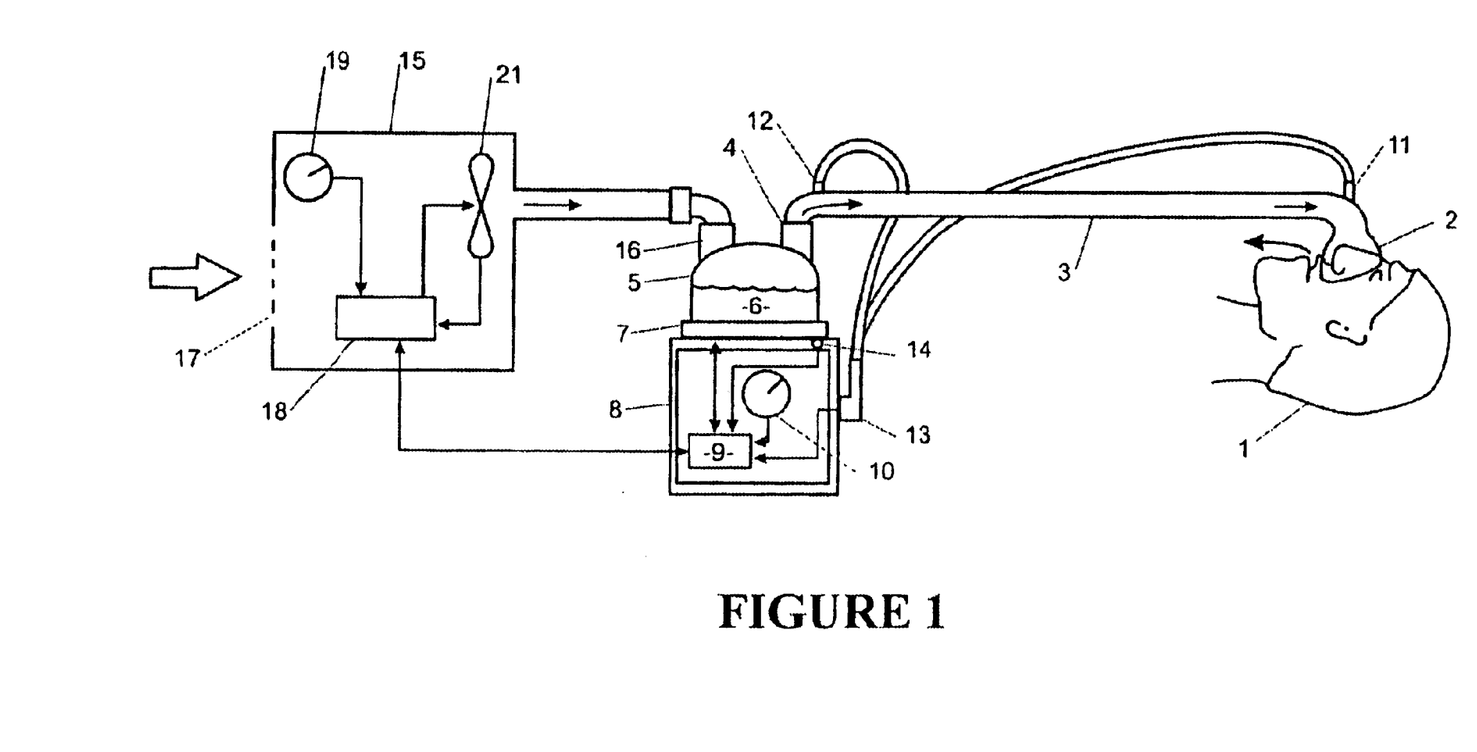
FIG. 1 is a block diagram of a humidified continuous positive airway pressure (CPAP system) as might be used in conjunction with the present invention.

With reference to FIG. 1 a humidified Continuous Positive Airway Pressure (CPAP) system is shown in which a patient 1 is receiving humidified and pressurised gases through a nasal mask 2 (or other types of patient interface as appropriate) connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 2:
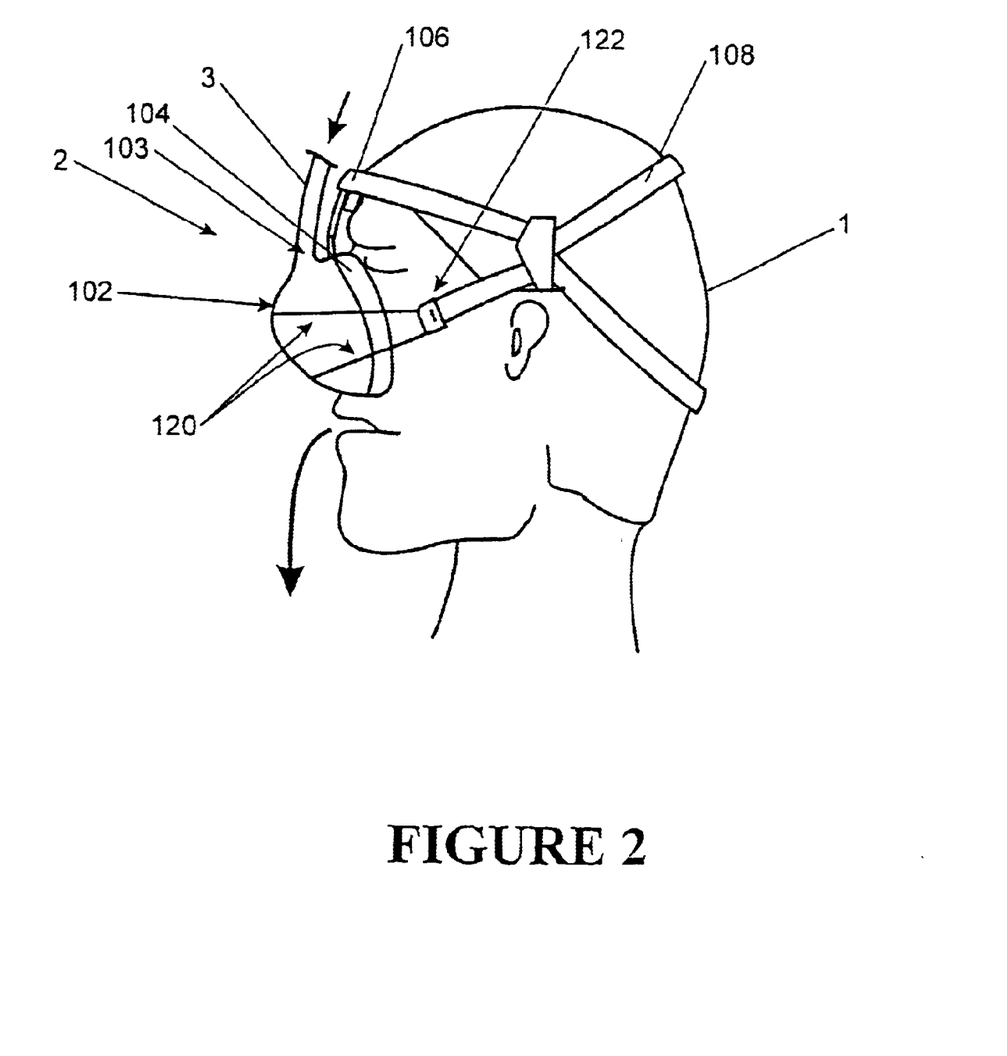
FIG. 2 is an illustration of the nasal mask in use according to the preferred embodiment of the present invention.

Referring to FIG. 2 the nasal mask, according to the preferred embodiment of the present invention, is shown in detail. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases in the preferred embodiment of the present invention are expelled through a valve in the mask 300, or alternatively a further expiratory conduit (not shown), or any other such method as is known in the art.

Mask Headgear

Figure 3:
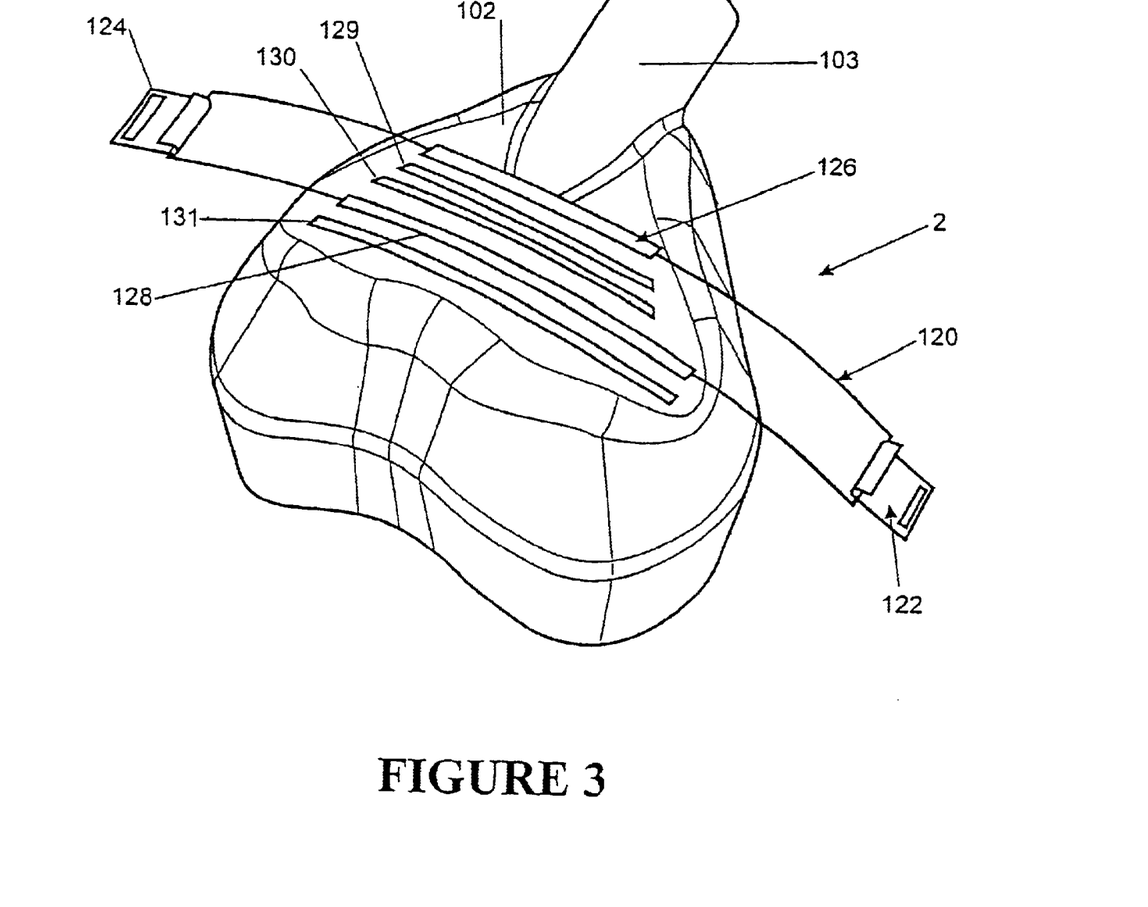
FIG. 3 is a front view of the nasal mask illustrating the headgear securement to the mask.

Referring now to FIGS. 2 and 3 the headgear 108 is shown connected to the hollow body 102. Rather than traditional fixed or adjustable attachments the present invention utilises a sliding engagement between the headgear 108 and the hollow body 102. This is achieved with a loop 120, running through harnessing clips 122, 124 on either side of the headgear 108 and over the top of the hollow body 102. The loop 120 is reciprocally engaged with guides 126, 128 mounted on the top surface of the hollow body 102. The guides constrain the loop 120 but allow it to slide in and out, meaning the headgear 108 can move laterally, independently of the hollow body 102.

The advantage to this is as the face is contorted during various sleeping positions the headgear is able to move with the changes in position while the mask is left in the correct position on the nose of the user and an effective seal is maintained.

Additional guides 129, 130, 131 allow the user to adjust position of loop 120, giving ability to get different pressure on the seal depending on loop 120 position.

To further ensure user comfort and effective pressure on the mask cushion 104, the headgear 108 may be constructed either using two straps running around the back of the user's head as shown in FIG. 2 or with a partial skull cap or any other configurations as are known in the art. In this case the straps or partial skull cap would be constructed using neoprene but may also be constructed using any material as is known in the art which will be comfortable for the user.

Figure 4:
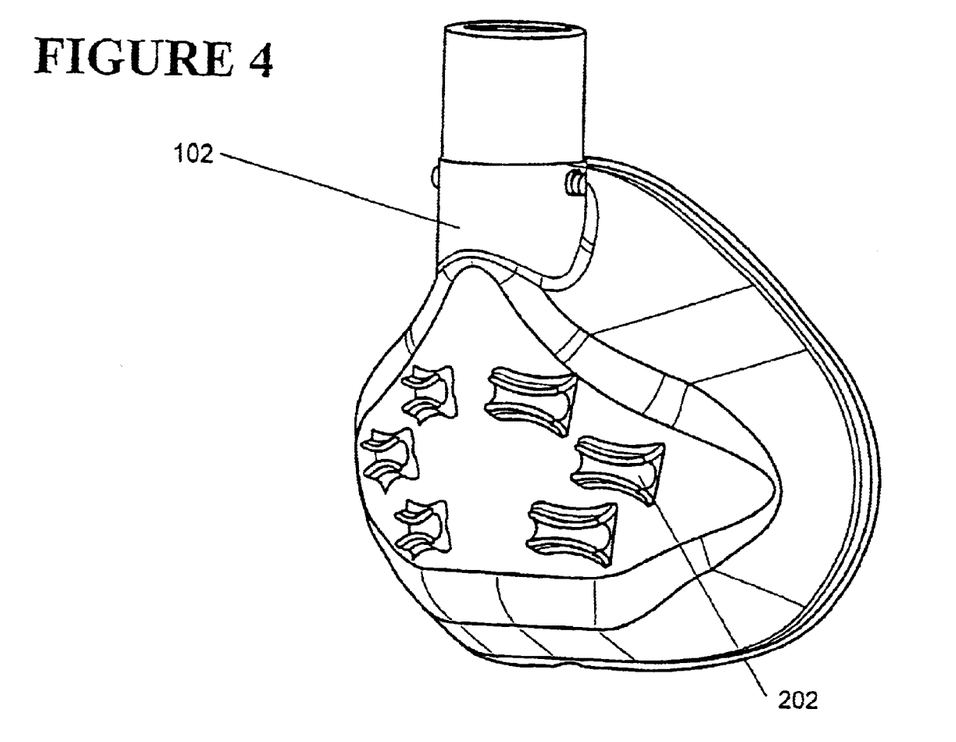
FIG. 4 is a perspective view of the mask illustrating the plurality of engaging clips to connect to the sliding strap
Figure 5:
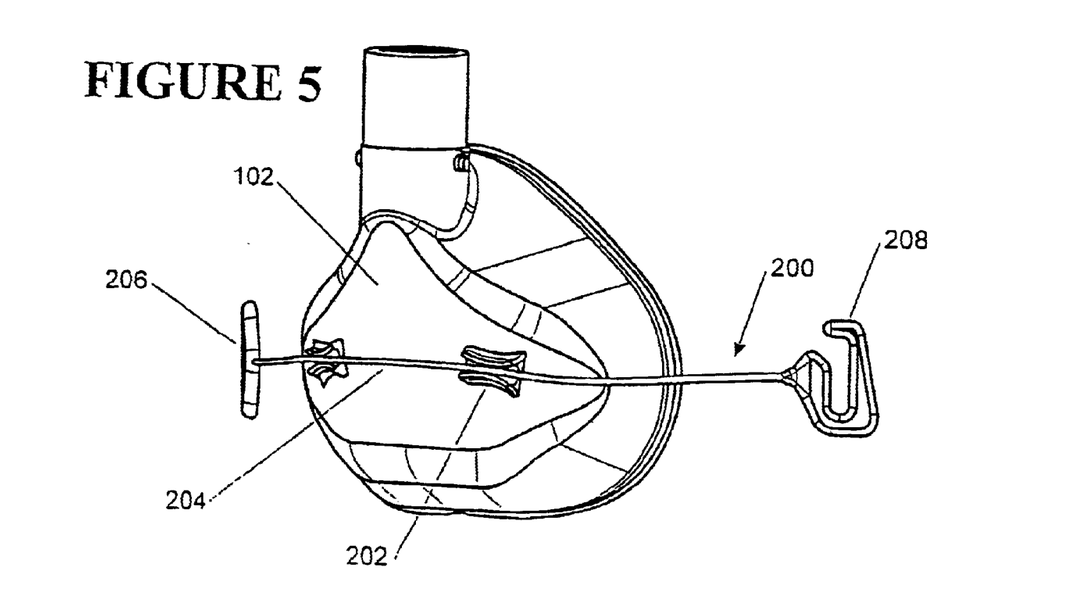
FIG. 5 is a perspective view of the mask showing the sliding strap clipped into the engaging clips.
Figure 6:
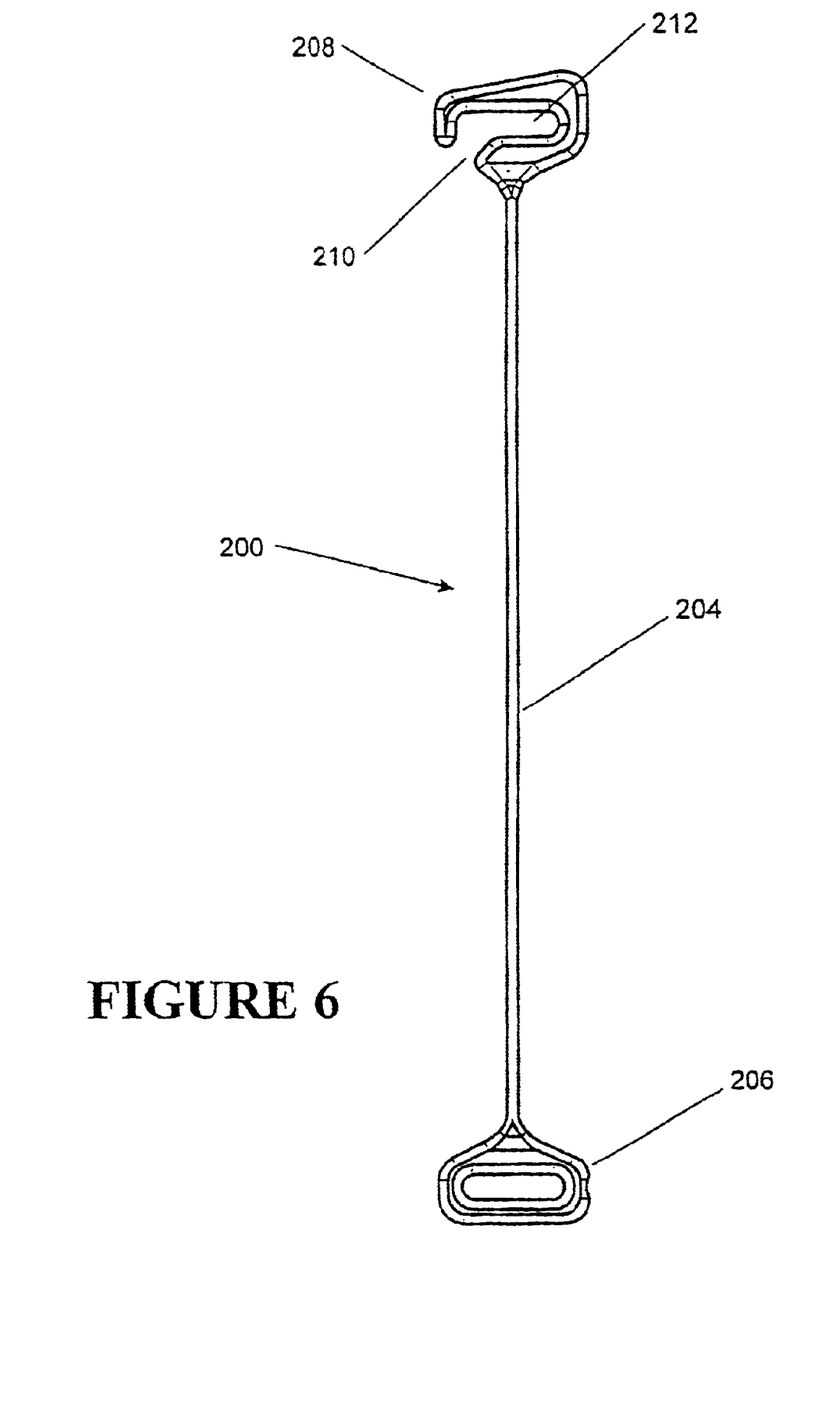
FIG. 6 is a side view showing the sliding strap.

In a further embodiment shown in FIGS. 4, 5 and 6 the present invention is illustrated using a sliding strap to attach the headgear 108 to the hollow body 102. The strap 200, shown in FIG. 6 in isolation, is constructed of polyacetal (Delrin 500P NC010) using injection moulding techniques to give a polished finish. This material, similar to other nylon based derivatives, with its polished finish has a particularly low friction co-efficient, slides with respect to the hollow body 102 with very little resistance.

As shown in FIG. 4, the hollow body 102 includes a number of engaging clips 202, in use the sliding strap 200 snaps into place into the engaging clips 202 and can only be removed therefrom using a substantial force. This means that with any normal use the sliding strap 200 will stay retained within the engaging clips 202. It will also be appreciated from FIG. 4 that a number of clips are so provided, in order to allow pressure from different angles for different face shapes.

As shown in FIG. 6 the sliding strap includes a midsection 204 intended to reciprocate with the engaging clips 202, terminated at each end by loops 206, 208 which attach to the headgear. The first loop 206 is a full loop through which the headgear 108 is permanently attached with for example, a velcro strap. The loop 208 at the other end, is only a partial loop 210 designed so that a strap or loop from the headgear 108 can be easily slipped in or out of the open section 212 to allow easy removal and attachment of the mask.

Outlet Vent

Figure 7:
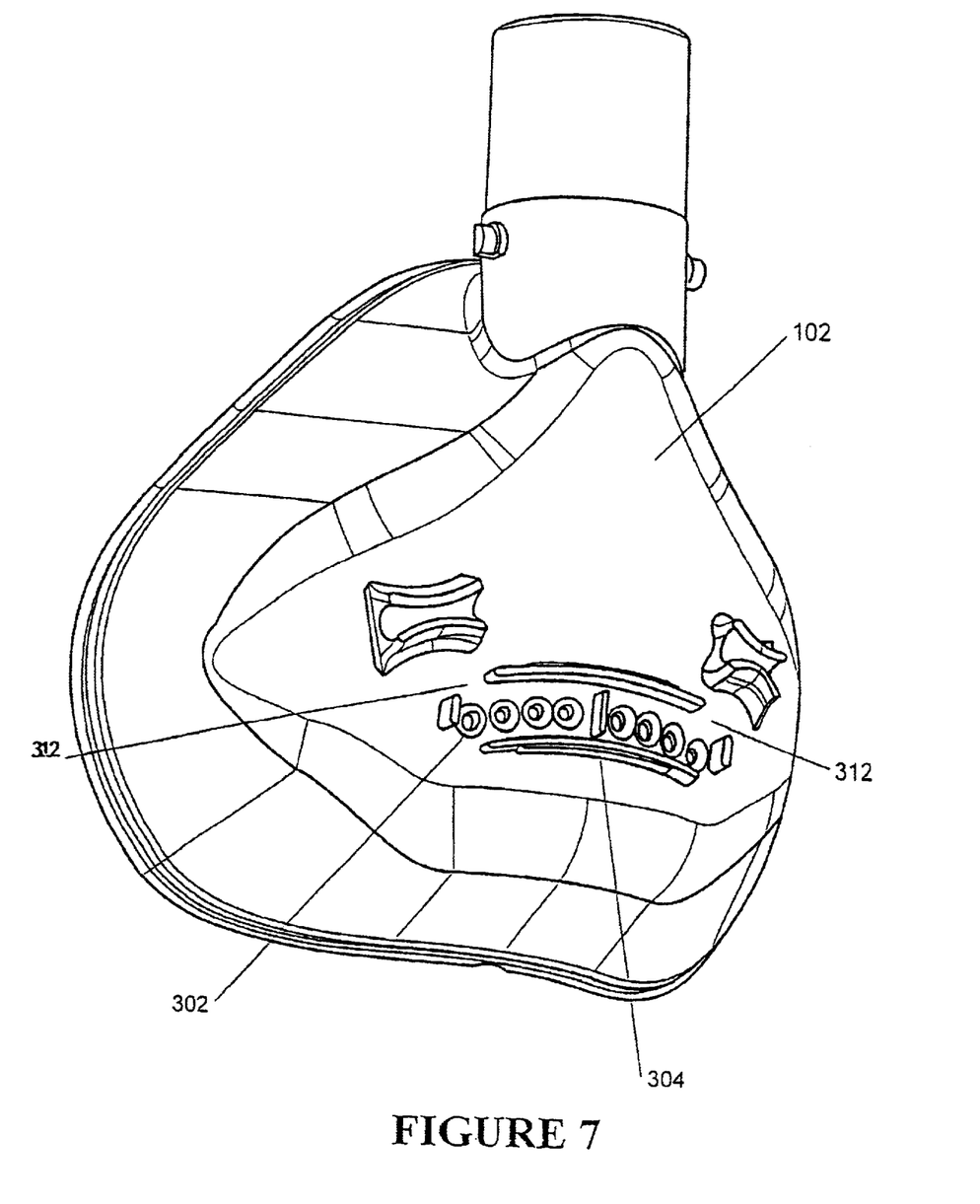
FIG. 7 is a perspective view of the mask illustrating the outlet vents.
Figure 8:
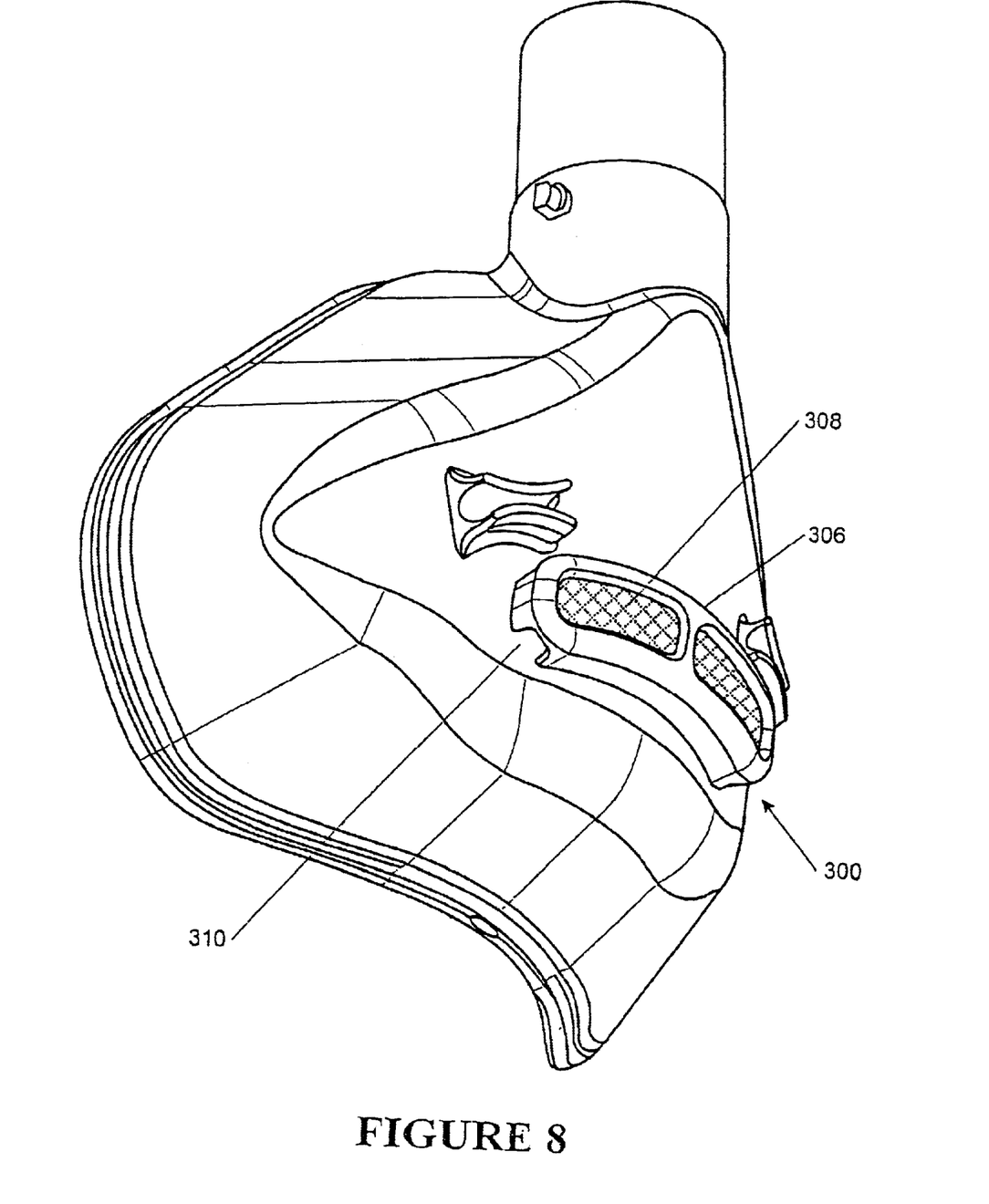
FIG. 8 is a perspective view of the mask illustrating the vent cap in place.
Figure 9:
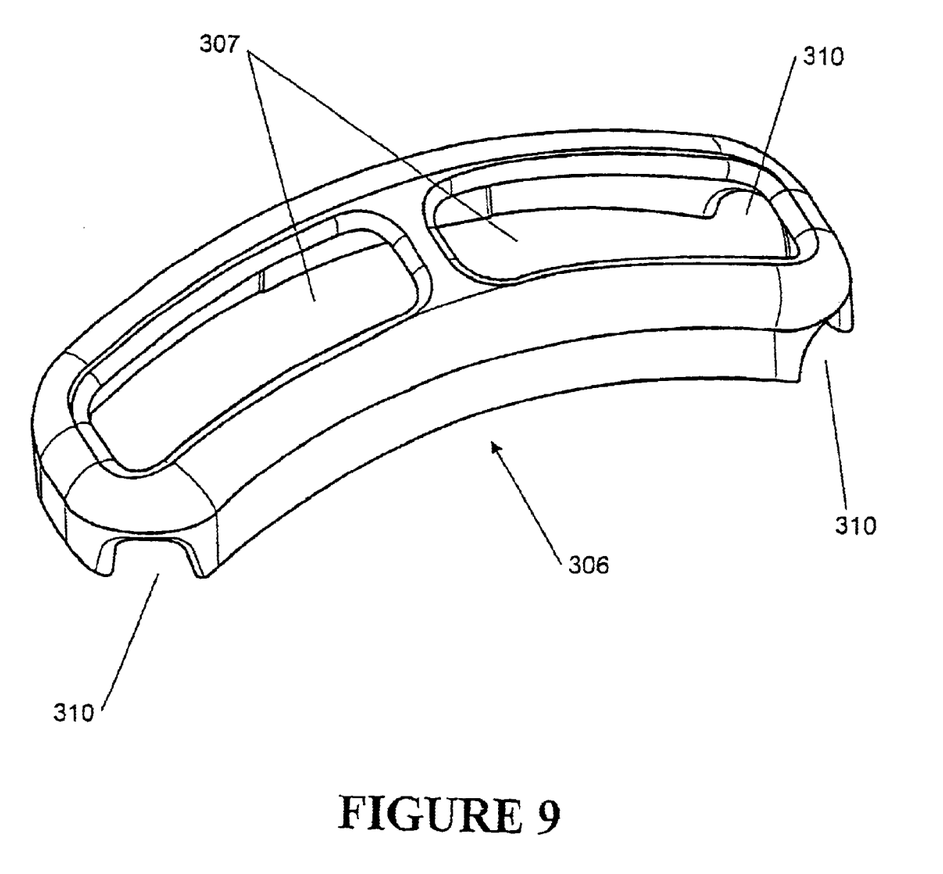
FIG. 9 is a perspective view of the vent cap.

In a further improvement shown in FIGS. 7 to 9 the present invention includes an outlet vent 300 as part of the body portion. The outlet vent 300 includes a number of apertures 302 either moulded in the body portion 102 or drilled through after moulding. The apertures 302 are separated and to some extent surrounded by a number of partitions 304 which provide support for a filter cap which is installed over top of the apertures 302.

The filter cap is designed primarily prevent what would otherwise be the noise generated from the flow of gases through the apertures 302 externally. This filter cap comprises a frame member 306 (shown in FIG. 9) which snaps on over top of the partition 304 and holds in place a piece of filter medium 308 which sits over top of the partitions 304. The frame 306 includes large vents 307 such that the expiratory or bias flow from the mask flows out the apertures 302 through the filter medium 308 and out the vent 307. The piece of filter medium 308 is preferably Ecofilt brand filter medium (PM135) which is less prone to blocking from the humidity levels often found in such applications.

The structure of the outlet vent allows for the filter medium to be replaced as and when necessary in an easy and efficient manner. The frame 306 can be easily removed, the filter medium 308 replaced and the frame 306 snapped on back in place. Further in the rare event of the filter medium blocking, auxiliary vents 310 are provided in the frame 306 which match up with gaps 312 in the partitions 304. As the auxiliary vents 310 are much smaller than the main vents 307 during normal use very little flow passes through them. If the filter medium 108 becomes blocked the flow is then forced through the auxiliary vents 310. This will be significantly more noisy than normal and will indicate the need for maintenance to the user.

It will be appreciated that by providing such a system the present invention effectively minimises the noise generated by the outward flow of expiratory gases from the mask. The present invention is of a low maintenance type and when replacement of the filter medium is required, it is an easy and simply exercise. As well as reducing the noise level the flow through the outlet vent is more diffused. This avoids for example, a flow of gases directed at a sleeping partner or a similar flow directed at the patient, either of which causing restlessness or waking.

The claims defining the invention are as follows:

1. In a device for delivering a supply of gases to a user comprising:
   a patient interface, in use in fluid communication with said supply of gases and supplying said gases to said user, and at least one outlet vent integrated with or in adjacent fluid communication the improvement comprising a diffusing member adapted to in use cover said vent, and to in use diffuse and audibly muffle a substantial portion of the expired gases of said user, where at least part of said member is porous and allows said substantial portion of said expired gases to pass through said member.

2. In a device for delivering a supply of gases to a user as claimed in claim 1 the improvement further comprising said diffusing member being removable.

3. In a device for delivering a supply of gases to a user as claimed in claim 2 the improvement further comprising said at least one outlet vent including at least one low resistance outlet and at least one high resistance outlet through which the expired gases of said user flow out through.

4. In a device for delivering a supply of gases to a user as claimed in claim 3 the improvement further comprising during normal use the majority of said expired gases passing from said at least one outlet vent and out through said low resistance outlet, whereby if the majority of said expired gases are substantially prevented from passing through said low resistance outlet, the majority of said expiratory gases passing out said high resistance outlet.

5. In a device for delivering a supply of gases to a user as claimed in claims 3 or 4 the improvement further comprising said high resistance outlet being comprised of apertures in said patient interface or said removable member or between said patient interface and said removable member.

6. In a device for delivering a supply of gases to a user as claimed in claims 3 or 4 the improvement further comprising said high resistance outlet being adapted such that in use is said low resistance outlet is blocked or has significant increase in resistance, and said high resistance outlet vents a sufficient flow of gases so as to prevent rebreathing of carbon dioxide by said user.

7. In a device for delivering a supply of gases to a user as claimed in claims 3 or 4 the improvement further comprising said removable member comprising a frame member and a disposable medium in use juxtaposed between said frame member and said at least one outlet vent, said low resistance outlet comprising the flow of said expired gases through said disposable medium.

8. In a device for delivering a supply of gases to a user as claimed in claim 7 the improvement further comprising said disposable medium reducing the external audible noise level and diffusing the flow pattern that would otherwise occur from said gases flowing through said at least one outlet vent.

9. In a device for delivering a supply of gases to a user as claimed in claim 7 improvement further comprising said disposable medium being a filter material.

10. In a device for delivering a supply of gases to a user as claimed in any of claims 1 to 4 wherein said patient interface comprises a mask having a hard body portion, an inlet to said body portion receiving said supply of gases, mask seal engaged with said body portion, and adapted to seal against the facial contours of said user, and means of securement to said user providing a compressive force on said mask seal to ensure said supply of gases is delivered to a user without significant leakage, said vent comprising at least one aperture in said body portion.

11. In a CPAP system for delivering gases to a user including a pressurized source of gases, gases transport means in fluid communication with said pressurized source adapted to convey said gases, and a patient interface in fluid communication with said transport means in use delivering said gases to said user, said patient interface including:
   gases outlet means having at least one outlet vent, and a diffusing member covering said vent, said outlet means in use passing, diffusing and audibly muffling a substantial portion of the expired gases of said user, where at least part of said member is porous and allows said substantial portion of said expired gases to pass through said member.

12. In a CPAP system as claimed in claim 11 the improvement further comprising said patient interface is a nasal mask.

13. A diffusing member for covering at least one vent in or adjacent a gases delivery patient interface comprising: a body adapted to in use pass, diffuse and audibly muffle a substantial portion of expired gases from a user and; means for removably connecting said body on or over a vent in or adjacent a gases delivery patient interface, wherein said diffusing member is porous.

14. A diffusing member as claimed in claim 13 where said diffusing member is removable.

15. A diffusing member as claims in claim 13 or 14, wherein said body includes a frame member and a disposable medium, said disposable medium adapted to be juxtaposed in use between said frame member and said at least one vent, and in use a low resistance outlet being formed by the flow of expired gases through said disposable medium, said removable diffusing member further comprising a high resistance outlet for the flow of expired gases if said low resistance outlet in use becomes blocked.

16. A diffusing member as claimed in claim 15 wherein said disposable medium is a filter material.

* * * * *

UNITED STATES PATENT AND TRADEMARK OFFICE
CERTIFICATE OF CORRECTION

PATENT NO. : 6,662,803 B2  
DATED : December 16, 2003  
INVENTOR(S) : Lewis George Gradon et al.

It is certified that error appears in the above-identified patent and that said Letters Patent is hereby corrected as shown below:

<u>Column 6,</u>  
Line 55, " as claims in" should read -- as claimed in --

Signed and Sealed this

Sixteenth Day of March, 2004

JON W. DUDAS  
*Acting Director of the United States Patent and Trademark Office*

UNITED STATES PATENT AND TRADEMARK OFFICE
CERTIFICATE OF CORRECTION

PATENT NO. : 6,662,803 B2
DATED : December 16, 2003
INVENTOR(S) : Lewis George Gradon et al.

It is certified that error appears in the above-identified patent and that said Letters Patent is hereby corrected as shown below:

Title page,
Item [30], Foreign Application Priority Data, "WO    WO 9848879" should be -- WO    WO 9848878 --

Signed and Sealed this

Twentieth Day of July, 2004

JON W. DUDAS
*Acting Director of the United States Patent and Trademark Office*